United States Patent [19]

Uesaka et al.

[11] Patent Number: 5,183,656

[45] Date of Patent: Feb. 2, 1993

[54] DEODORANT AND PRODUCT IN WHICH THE DEODORANT IS USED

[75] Inventors: Kazuo Uesaka, Amagasaki; Kazumasa Okita, Ueno; Tsutomu Arai, Saitama, all of Japan

[73] Assignees: Mitsubishi Denki Kabushiki Kaisha, Tokyo; Okitsumo Incorporated, Mie, both of Japan

[21] Appl. No.: 739,433

[22] Filed: Aug. 2, 1991

[30] Foreign Application Priority Data

Aug. 3, 1990 [JP] Japan .................. 2-207389

[51] Int. Cl.$^5$ .................................. A61L 9/00
[52] U.S. Cl. ........................... 424/76.1; 424/47; 514/945
[58] Field of Search ............ 424/76.1, 47, 76.1; 514/945

[56] References Cited

U.S. PATENT DOCUMENTS

| 4,938,957 | 7/1990 | Iwahashi | 424/76.1 |
| 5,008,103 | 4/1991 | Raleigh et al. | 424/47 |
| 5,034,222 | 7/1991 | Kellett et al. | 514/945 |

FOREIGN PATENT DOCUMENTS

| 0024175 | 8/1980 | European Pat. Off. |
| 64-58978 | 3/1989 | Japan. |
| 1189321 | 7/1989 | Japan. |

*Primary Examiner*—Thurman K. Page
*Assistant Examiner*—William E. Benston, Jr.
*Attorney, Agent, or Firm*—Oblon, Spivak, McClelland, Maier & Neustadt

[57] ABSTRACT

A deodorant comprising an organosilicon as binder and a metal oxide or salt of at least one member selected from the group consisting of titanium, zirconium, lanthanum and manganese.

9 Claims, 1 Drawing Sheet

DEODORANT AND PRODUCT IN WHICH THE DEODORANT IS USED

The present invention relates to a deodorant to be used mainly for household electrical equipments such as kitchen utensils and housing equipments and designed to deodorize a bad odor of e.g. an amine, mercaptan, indole or skatole by a catalyst, and a product in which such a deodorant is used.

In an electronic oven or a refrigerator which is commonly used in a kitchen, a bad odor substance such as an amine, mercaptan, indole or skatole is formed by a modification of an oil scattered during cooking or by a modification of the food product itself. When such a bad odor is formed, it has heretofore been common to wait until the bad odor is naturally dissipated or to conduct deodorization by adsorption on e.g. active carbon. Further, with respect to a refrigerator, a deodorizing method by means of ozone or a photocatalyst has been proposed recently in Japanese Unexamined Patent Publication No. 58978/1989 or No. 189321/1989. However, in either case, there has been drawbacks such that the deodorizing effects are poor, the effective life is rather short, and an apparatus of a large scale is required.

As a means for effectively deodorizing a bad odor substance, it is commonly known to decompose the bad odor substance by means of a catalyst such as a metal oxide.

However, such a method has the following problems:

(1) The decomposition by oxidation or reduction of the bad odor by means of a catalyst is not so effective at a low temperature of not higher than 200° C., and it takes time for deodorization at such a low temperature.

(2) In order to effectively deodorize the bad odor, it is necessary to adequately contact the catalyst with the gaseous bad odor substance, but it is difficult to hold the catalyst for this purpose.

(3) Further, it is necessary to guide the gaseous bad odor substance to the catalyst in order to contact the bad odor substance to the catalyst, but an apparatus for such guidance tends to be of a large scale.

The present invention has been made to solve such problems, and it is an object of the present invention to provide a deodorant having good deodorizing effects.

Another object of the present invention is to obtain a deodorant which has suitable cracks so that the contact of the catalyst having deodorizing effects with the bad odor will be adequate and which is durable for use even under a severe condition for a long period of time without substantial deterioration by heat or ultraviolet rays.

A further object of the present invention is to provide a deodorant wherein the ratio of the solid content to the solvent in the deodorant is the same as in a conventional coating material which is commonly employed and of which the viscosity can be made substantially the same as a conventional coating material, so that the conventional coating technique can be used without change.

A still further object of the present invention is to provide a deodorant which has a wettability even to an inactive surface to secure adhesion, whereby even when the object to be coated has an inactive surface such as stainless steel, a coating having adequate adhesion can be obtained.

Another object of the present invention is to provide a product using the above deodorant, which is not required to be of such a large scale as required heretofore.

According to the first aspect, the present invention provides a deodorant comprising an organosilicon as binder and a metal oxide or salt of at least one member selected from the group consisting of titanium, zirconium, lanthanum and manganese.

According to the second aspect, the present invention provides a deodorant comprising an inorganic silicon as binder and a metal oxide or salt of lanthanum.

According to the third aspect, the present invention provides a deodorant comprising an organosilicon and an inorganic silicon as binder and a metal oxide or salt of at least one member selected from the group consisting of titanium, zirconium, lanthanum and manganese.

According to the fourth aspect, the present invention provides a deodorant comprising from 5 to 98 wt % of the above-mentioned binder, from 0.50 to 90 wt % of a metal oxide or salt of at least one member selected from the group consisting of titanium, zirconium, lanthanum and manganese, from 0 to 94.5 wt % of a colorant and/or a filler, and from 0.5 to 5 wt % of an additive.

According to the fifth aspect of the present invention, the additive for the above deodorant is a fluorine type wetting agent and/or an anti-settling agent of polyethylene oxide type or organic amide type.

According to the sixth aspect, the present invention provides a product having the above-mentioned deodorant coated on a wall surface to be exposed to a bad odor or in a bad odor pathway, and thus having a deodorizing function imparted.

Now, the present invention will be described in detail with reference to the preferred embodiments.

In the present invention, the metal oxide or salt of e.g. titanium, zirconium, lanthanum or manganese, provides a deodorizing function without impairing the curing of the binder.

In another aspect of the present invention, the additive has a wettability even against an object having an inactive surface so that adhesion can thereby be secured, and it is possible to obtain a coating having adequate adhesion even when the object to be coated has an inactive surface such as stainless steel.

Further, according to another aspect of the present invention, an inorganic silicon and an organic silicon are properly blended as binder, and curing is conducted under prescribed curing conditions to form suitable cracks so that the contact of the catalyst having a deodorizing function with the bad odor will be adequate, and the deodorant is durable for use under a severe condition for a long period of time without substantial deterioration by heat or ultraviolet rays.

Further, according to another aspect of the present invention, the ratio of the solid content to the solvent in the deodorant is adjusted to be the same as a conventional coating material which is commonly employed, whereby the viscosity will be substantially the same as the conventional coating material, and the conventional coating technique may be applied without change.

By the above function, when the deodorant of the present invention is used as a coating material, it is possible to obtain a deodorizing coating material having excellent coating properties and good adhesion. Further, a deodorizing coating material having excellent deodorizing effects and being excellent in the selectivity of the base material can be obtained, whereby it is possible to attain a deodorizing coating having excellent productivity and good adhesion to various substrates.

Now, the present invention will be described in further detail with reference to Examples. However, it should be understood that the present invention is by no means restricted to such specific Examples.

BRIEF DESCRIPTION OF THE DRAWING

In the accompanying drawing.

Figure 1:
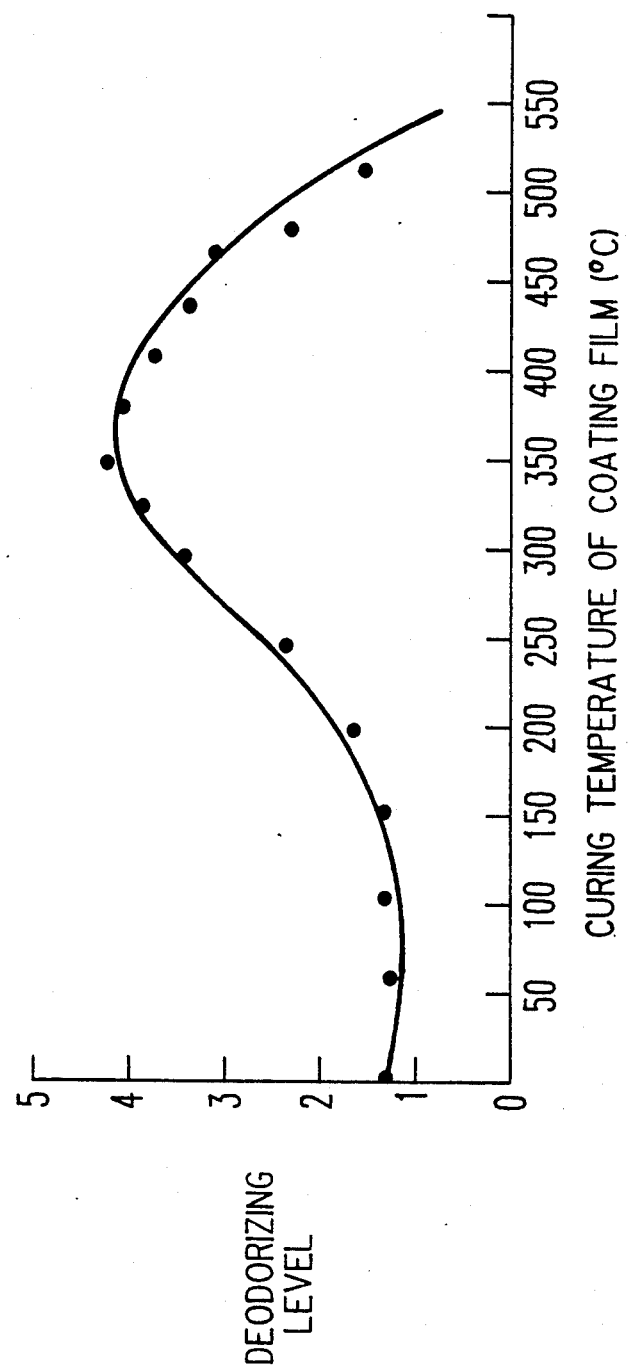
FIG. 1 is a characteristic graph showing the change in the deodorizing rate due to the curing temperature of the coating material.

Table 1 shows the results of overall evaluation relating to the properties of various binder materials. Here, binder (1) is an organosilicon (such as KR-311, tradename, manufactured by Shinetsu Chemical Company Ltd.), binder (2) is an inorganic silicon (such as ethanol silica sol, manufactured by Nissan Chemical Industries Co., Ltd.), binder (3) is a mixture comprising ethylene tetrafluoride (average molecular weight: about 3,000) and the inorganic silicon of binder (2) (mixing ratio of 1:40), binder (4) is a bisphenol type epoxy resin (average molecular weight: about 1,800), binder (5) is a copolymer (average molecular weight: about 2,200) of polyether sulfide and propylene hexafluoride, binders (6) to (14) are mixtures of the organosilicon of binder (1) and the inorganic silicon of binder (2) in various blend ratios as identified in the Table. Here, as the metal oxide or salt, titanium oxide and zirconium phosphate were used. The metal oxide or salt was used in an amount of 100 parts by weight per 100 parts by weight of the binder to obtain a coating material. As the additive, a wetting dispersant for the metal oxide or salt, a leveling agent for the binder or an adhesion-improving agent was incorporated in an amount of 0.5 part by weight. The substrate used for this evaluation was standard stainless steel plate (SUS304; thickness: 0.5 mm). Coating was conducted by a usual air spray gun (such as W-71, manufactured by Iwata Tosoki K. K.) under a discharging pressure of 4 kg/cm$^2$ to obtain a coating layer having a thickness of 25 μm. The viscosity of the coating material at this time was adjusted to 55 cps. Here, as a viscosity-controlling agent for the coating material, xylene was used. With respect to the curing conditions for the coating material, an electric oven was used which is capable of controlling the furnace temperature with a precision of ±3° C., and every sample was dried at 80° C. for 10 minutes, followed by curing for 20 minutes at 190° C. in the case of binder (4) and at 60° C. in the case of other binders.

Table 2 shows the results of evaluation of the effects of the additives. Here, additives (1), (2) and (3) are a metal oxide or salt, a colorant and a wetting dispersant for a filler. Namely, additive (1) is a fluorine type polymer (such as a nonionic type), additive (2) is a halogen-containing surfactant (such as a nonionic type), and additive (3) is a non-polar polymethylene type (anionic type). Additives (4), (5) and (6) are leveling agents. Namely, additive (4) is a high boiling point ether (e.g. boiling point: 246° C.), additive (5) is an organopolysiloxane type (boiling point: 139° C.), and additive (6) is a non-silicone type unsaponifiable material (refractive index: 1.441). Further, additives (7) and (8) are adhesion-improving agents. Namely, additive (7) is a silane coupling agent (TSL-8340), and additive (8) is an organic functional silane ester (boiling point: 117° C.). Additive (9) is a coating film-improving agent, which is a mixture of an organic silicone and a high boiling point ether (ST94PA). Further, additives (10), (11) and (12) are anti-settling agents which prevent settling of the metal oxide or salt, the coloring material or the filler contained in the deodorant. Namely, additive (10) is a polyethylene oxide type (average molecular weight: 800), and additives (11) and (12) are organic amides (average molecular weight: 1,100). For this evaluation, a mixture of binder (1) and (2) was used as binder. Other conditions were the same as the evaluation of binders.

Table 3 shows the results of examination of the curing properties due to a difference in the blend ratio of the metal oxide or salt, the colorant and the filler to the binder. As the colorant, a metal oxide type black and red were used. As the filler, titanium type, magnesium type and aluminum type fillers were used. As the binder, binder (8) which is a mixture of an organosilicon and an inorganic silicon, was used. The curing conditions were the same as in the evaluation of the binders.

Table 4 shows the results of evaluation of the deodorizing effects of the metal oxide or salt used as a deodorizing catalyst against trimethylamine, methane thiol (methylmercaptan) and hydrogen sulfide. Here, catalyst (1) is a zeolite type, catalysts (2) and (3) are active alumina type, (e.g. 200 mesh), catalyst (4) is a platinum type, catalyst (5) is silica gel, catalysts (6) to (9) are active carbon (such as coconut shell active carbon: 4–10 mesh), catalyst (10) to (14) are molecular sieves (e.g. 6A), catalyst (15) is a lanthanum type, catalysts (16) to (18) are titanium type (such as titanium dioxide having a particle size of from 5 to 15 μm), catalysts (19) and (20) are manganese type (such as manganese dioxide), catalyst (21) is a beryllium type, catalyst (22) is a lithium type, catalysts (23) and (24) are a zinc type (such as zinc oxide), catalyst (25) is lead oxide, catalyst (26) is a cupric oxide, catalyst (27) is chromium oxide, catalysts (28) to (31) are tin type (such as stannous oxide), catalyst (32) is antimony trioxide, catalyst (33) is a strontium type, catalyst (34) is nickel monooxide, catalyst (35) is a boron type, catalysts (36) to (41) are silicon type (such as silicon dioxide), catalyst (42) is an iron type, catalysts (43) to (46) are a zirconium type (such as zirconium phosphate), catalysts (47) to (50) are a magnesium type (such as magnesium fluoride), catalyst (51) is a cobalt type, catalyst (52) is a barium type, catalysts (53) to (56) are a calcium type (such as calcium oxide), catalysts (57) to (59) are aluminum type (such as condensed aluminum phosphate), catalyst (60) is copper chromate, catalyst (61) is titanium yellow, catalysts (62) to (74) are mixtures of metal oxides (such as talc) and catalysts (75) to (78) are metal powders (such as metal manganese powder).

Table 5 shows the results of examination of the curing temperature of the coating film. Here, the coating material used was a mixture comprising 100 parts by weight of binder (8) (which is a mixture of binders (1) and (2)) and 100 parts by weight of a metal oxide or salt of each of titanium type, manganese type, zirconium type and lanthanum type, red and black colorants of metal oxides, and titanium type, magnesium type and aluminum type fillers. With respect to the curing conditions, the natural drying was conducted by leaving a sample in a constant temperature room set at a predetermined temperature, and forcible drying or baking drying conditions were the same as in the evaluation of binders.

In the Tables, symbol ⊙ indicates that the properties are excellent, ○ indicates that the properties are good, Δ indicates that the properties are practically useful, and symbol x indicates that the properties are not practically useful.

FIG. 1 of the drawing is a characteristic graph showing the change in the deodorizing rate due to the curing temperature of the coating material, in which the ordinate represents the deodorizing level, and the abscissa indicates the curing temperature (°C.) of the coating film. For this study, binder (8) which is a mixture of binders (1) and (2) was used as the binder. Further, as the deodorizing catalyst, each of titanium type, manganese type, zirconium type and lanthanum type was used.

As a result of the foregoing evaluations, it has been found that even binder (3) which is a mixture of ethylene fluoride and an inorganic silicon may be used as binder without any practical problem. However, in order to secure adhesion, it is preferred to employ an organosilicon, and in order to form suitable cracks to improve the contact with the catalyst, it is preferred to employ an inorganic silicon. Accordingly, in order to obtain good deodorizing effects as a coating material for an object having a low surface activity, it is preferred to employ binders (7) to (12) which are mixtures of an organosilicon and an inorganic silicon. Among them, binder (8) has constant properties in respect of various characteristics, and thus it is preferred to employ binder (8) in order to obtain a good deodorizing coating material.

As the additive, it is possible to employ additive (1) which is a fluorine type wetting dispersant, additive (4) which is a leveling agent of a high boiling ether type, additive (6) which is a leveling agent of a non-silicone type unsaponifiable material, additive (8) which is an adhesion-improving agent of an organic functional silane ester type, additive (10) which is an anti-settling agent of polyethylene oxide type and additive (11) which is an anti-settling agent of an organic amide type. From the viewpoint of the cost of the coating material and the effects of use, it is preferred to employ additive (1) which is a fluorine-type wetting dispersant, additive (10) which is an anti-settling agent of polyethylene oxide type or additive (11) which is an anti-settling agent of an organic amide type.

The metal oxides or salts used as a deodorizing catalyst are all effective for deodorizing a part or whole of trimethylamine, methane thiol and hydrogen sulfide. However, those having particularly effective among them are catalyst (6) which is active carbon, catalyst (15) of a lanthanum type, catalysts (16), (17) and (18) of a titanium type, catalyst (23) of a zinc-type, catalyst (37) of a silicon type, catalysts (43) and (45) of a zirconium type, and catalysts (67) and (72) which are metal oxides.

With respect to the blend ratio of the binder and the fillers including the metal oxide, the salt, the colorant and the bulking filler, such fillers may be employed under a stabilized condition within a range of from 19 to 0.01 part by weight per one part by weight of the binder. However, most preferably, the fillers are in an amount within a range of from 3 to 0.3 part by weight relative to one part by weight of the binder.

Further, when the deodorants of the Examples of the present invention are used as coating materials, the curing conditions may be within a range of from 25° C. at 8 hours to 420° C. for 20 minutes. However, in view of the durability of the coating film and the deodorizing effects, the curing conditions are most preferably within a range of from 250° C. for 20 minutes to 400° C. for 20 minutes. Therefore, coating materials were prepared so that coating films have blend compositions as identified in Table 6. As a result, good coating films were obtained with Blend Examples 7 and 11.

In a case where the deodorants of the Examples of the present invention are used as coating materials, if the viscosity of such coating materials is adjusted to be the same as the viscosity of conventional coating materials, it is possible not only to apply the conventional coating technique whereby there is no substantial restriction from the viewpoint of the production, but also to use the existing installation, whereby the cost for investment to installation can be saved. Further, with such coating materials, wet-on-wet coating is possible, and it is easy to mend a defective coating during the coating operation or after the final inspection, whereby it is possible to improve the yield.

As described in the foregoing, according to the present invention, deodorants having excellent deodorizing effects can be obtained by using an organosilicon as binder and incorporating thereto at least one metal oxide or salt of titanium, zirconium, lanthanum and manganese, or using an inorganic silicon as binder and incorporating thereto a metal oxide or salt of lanthanum.

According to another aspect of the present invention, it is possible to obtain a deodorant which has suitable cracks whereby the contact between the deodorizing catalyst and a bad odor will be adequate and which is durable for use under a severe condition for a long period of time without substantial deterioration by heat or ultraviolet rays, by using an organic silicon and an inorganic silicon as binder and incorporating thereto at least one metal oxide or salt of titanium, zirconium, lanthanum and manganese.

According to another aspect of the present invention, it is possible to obtain a deodorant wherein the ratio of the solid content to the solvent in the deodorant is the same as a conventional coating material commonly employed and the viscosity can be made substantially the same as the conventional coating material so that the conventional coating technique can be used without change, by using a deodorant which comprises from 5 to 98 wt % of the binder, from 0.50 to 90 wt % of a metal oxide or salt of at least one member selected from the group consisting of titanium, zirconium, lanthanum and manganese, from 0 to 94.5 wt % of a colorant and/or a bulking filler and from 0 to 5 wt % of an additive.

According to another aspect of the present invention, it is possible to obtain a deodorant which has wettability even against an object having an inactive surface and which is capable of providing a coating having adequate adhesion even on an object having an inactive surface such as stainless steel, since the adhesion can thereby be secured.

According to a still further aspect of the present invention, it is possible to obtain a product which does not require a large installation as required before, by coating the above deodorant on a wall surface at the portion where a bad odor is present or in a bad odor pathway to impart a deodorizing function, whereby it is possible to readily provide a deodorizing function at a low cost to kitchen utensils such as an electronic oven and a refrigerator and household electrical products including housing products such as toilet fans or circulators as well as the products for automobiles such as car coolers and circulators.

TABLE 1

| | Film forming properties | Water resistance | Heat resistance | Adhesion | Blend ratio |
| --- | --- | --- | --- | --- | --- |
| Binder (1) | ○ | ○ | △ | ⊙ | |
| Binder (2) | △ | △ | ⊙ | ○ | |
| Binder (3) | ○ | ○ | ⊙ | ○ | |
| Binder (4) | ⊙ | ○ | x | ⊙ | |

TABLE 1-continued

|  | Film forming properties | Water resistance | Heat resistance | Adhesion | Blend ratio |
|---|---|---|---|---|---|
| Binder (5) | ○ | △ | △ | × |  |
| Binder (6) | ○ | △ | ○ | ○ | 8:1 |
| Binder (7) | ⊙ | ○ | ⊙ | ○ | 4:1 |
| Binder (8) | ⊙ | ⊙ | ⊙ | ⊙ | 3:1 |
| Binder (9) | ○ | ⊙ | ⊙ | ⊙ | 2:1 |
| Binder (10) | ○ | ○ | ⊙ | ⊙ | 1:1 |
| Binder (11) | ○ | ○ | ⊙ | ○ | 1:2 |
| Binder (12) | ⊙ | ○ | ○ | ○ | 1:3 |
| Binder (13) | ⊙ | ⊙ | △ | ○ | 1:4 |
| Binder (14) | △ | △ | ○ | ⊙ | 1:8 |

Blend ratio: Weight ratio of Binder (1):Binder (2)

TABLE 2

|  | Dispersibility | Leveling properties | Adhesion | Surface appearance | Stability of coating material |
|---|---|---|---|---|---|
| Additive (1) | ⊙ | — | ⊙ | △ | ⊙ |
| Additive (2) | △ | — | × | △ | ⊙ |
| Additive (3) | △ | — | × | ○ | ⊙ |
| Additive (4) | — | ⊙ | ⊙ | ⊙ | ⊙ |
| Additive (5) | — | ⊙ | △ | ⊙ | ○ |
| Additive (6) | — | ○ | ○ | ○ | ⊙ |
| Additive (7) | — | — | ⊙ | ○ | △ |
| Additive (8) | — | — | ⊙ | ○ | ⊙ |
| Additive (9) | — | — | △ | ⊙ | ○ |
| Additive (10) | — | — | ⊙ | ○ | ⊙ |
| Additive (11) | — | — | ⊙ | ○ | ⊙ |
| Additive (12) | — | — | △ | △ | ⊙ |

TABLE 3

|  | Blend ratio | Pencil hardness | Solvent rubbing | Flexibility | Deodorizing effects |
|---|---|---|---|---|---|
| Example (1) | 99 | 6H | × | × | ⊙ |
| Example (2) | 49 | 5H | ○ | × | ⊙ |
| Example (3) | 19 | 4H | △ | ○ | ⊙ |
| Example (4) | 9 | 4H | ⊙ | ○ | ⊙ |
| Example (5) | 3 | 3H | ⊙ | ○ | ⊙ |
| Example (6) | 1 | 3H | ⊙ | ⊙ | ⊙ |
| Example (7) | 0.3 | 2H | ⊙ | ⊙ | ○ |
| Example (8) | 0.1 | 2H | ⊙ | ⊙ | ○ |
| Example (9) | 0.05 | 2H | ⊙ | ⊙ | ○ |
| Example (10) | 0.02 | 2H | ⊙ | ⊙ | ○ |
| Example (11) | 0.01 | 2H | ⊙ | ⊙ | ○ |
| Example (12) | 0.005 | 2H | ⊙ | ⊙ | △ |

Blend ratio: The weight ratio of the metal oxide, the salt, the colorant and the bulking filler relative to 1 part by weight of the binder.

TABLE 4

|  | Trimethylamine | Methanthiol | Hydrogen sulfide |
|---|---|---|---|
| Catalyst (1) | ○ | × | △ |
| Catalyst (2) | × | × | ○ |
| Catalyst (3) | ○ | △ | △ |
| Catalyst (4) | △ | ○ | ○ |
| Catalyst (5) | ⊙ | ○ | ○ |
| Catalyst (6) | ○ | ⊙ | ⊙ |
| Catalyst (7) | ○ | ⊙ | ○ |
| Catalyst (8) | ⊙ | ○ | ○ |
| Catalyst (9) | ○ | ○ | ○ |
| Catalyst (10) | △ | △ | ○ |
| Catalyst (11) | △ | ○ | △ |
| Catalyst (12) | △ | △ | ○ |
| Catalyst (13) | ○ | △ | △ |
| Catalyst (14) | △ | × | △ |
| Catalyst (15) | ⊙ | ⊙ | ⊙ |
| Catalyst (16) | ⊙ | ⊙ | ⊙ |
| Catalyst (17) | ○ | ⊙ | ⊙ |
| Catalyst (18) | ⊙ | ○ | ⊙ |
| Catalyst (19) | ○ | ⊙ | ○ |
| Catalyst (20) | ⊙ | ⊙ | ○ |
| Catalyst (21) | × | △ | × |
| Catalyst (22) | × | × | × |
| Catalyst (23) | ⊙ | ○ | ⊙ |
| Catalyst (24) | △ | × | × |
| Catalyst (25) | △ | × | △ |
| Catalyst (26) | △ | ○ | ○ |
| Catalyst (27) | × | × | × |
| Catalyst (28) | ○ | ○ | ○ |
| Catalyst (29) | ○ | △ | ○ |
| Catalyst (30) | ○ | △ | ○ |
| Catalyst (31) | ○ | △ | × |
| Catalyst (32) | ○ | △ | △ |
| Catalyst (33) | ○ | × | △ |
| Catalyst (34) | △ | △ | △ |
| Catalyst (35) | △ | × | × |
| Catalyst (36) | △ | × | × |
| Catalyst (37) | ⊙ | ⊙ | ⊙ |
| Catalyst (38) | ⊙ | × | △ |
| Catalyst (39) | ○ | ○ | ○ |
| Catalyst (40) | △ | ○ | ○ |
| Catalyst (41) | ○ | ○ | ○ |
| Catalyst (42) | △ | × | × |
| Catalyst (43) | ⊙ | ○ | ⊙ |
| Catalyst (44) | △ | × | △ |
| Catalyst (45) | ⊙ | ⊙ | ⊙ |
| Catalyst (46) | ⊙ | ○ | ⊙ |
| Catalyst (47) | △ | △ | △ |
| Catalyst (48) | × | × | △ |
| Catalyst (49) | × | × | ○ |
| Catalyst (50) | × | × | × |
| Catalyst (51) | ○ | ○ | △ |
| Catalyst (52) | ○ | ○ | △ |
| Catalyst (53) | △ | ○ | ○ |
| Catalyst (54) | △ | ○ | ○ |
| Catalyst (55) | △ | ○ | ○ |
| Catalyst (56) | × | △ | × |
| Catalyst (57) | △ | ○ | △ |
| Catalyst (58) | ○ | ⊙ | ○ |
| Catalyst (59) | ○ | ○ | △ |
| Catalyst (60) | × | × | × |
| Catalyst (61) | ○ | ○ | △ |
| Catalyst (62) | ○ | ○ | △ |
| Catalyst (63) | ○ | ○ | ○ |
| Catalyst (64) | ○ | ○ | ○ |
| Catalyst (65) | ○ | ○ | ⊙ |
| Catalyst (66) | ○ | ○ | △ |
| Catalyst (67) | ⊙ | ○ | ⊙ |
| Catalyst (68) | ○ | ○ | ○ |
| Catalyst (69) | ○ | △ | △ |
| Catalyst (70) | ○ | ○ | △ |
| Catalyst (71) | ⊙ | ○ | △ |
| Catalyst (72) | ⊙ | ⊙ | ○ |
| Catalyst (73) | × | ○ | ○ |
| Catalyst (74) | × | × | ○ |
| Catalyst (75) | ○ | △ | △ |
| Catalyst (76) | ○ | ○ | △ |
| Catalyst (77) | × | × | × |
| Catalyst (78) | × | × | × |

TABLE 5

|  | Adhesion | Pencil hardness | Water resistance | Solvent rubbing | Flexibility |
|---|---|---|---|---|---|
| 5° C. × 8 hr | △ | 4B | × | × | ⊙ |
| 10° C. × 8 hr | △ | 2B | × | × | ⊙ |
| 15° C. × 8 hr | △ | HB | × | × | ⊙ |
| 20° C. × 8 hr | ○ | F | △ | △ | ⊙ |
| 25° C. × 8 hr | ○ | 2H | ○ | ○ | ⊙ |
| 80° C. × 20 min. | ○ | 2H | ○ | ○ | ⊙ |
| 100° C. × 20 min. | ○ | 2H | ○ | ○ | ⊙ |
| 150° C. × 20 min. | ⊙ | 2H | ⊙ | ⊙ | ⊙ |
| 200° C. × 20 min. | ⊙ | 2H | ⊙ | ⊙ | ⊙ |
| 250° C. × 20 min. | ⊙ | 2H | ⊙ | ⊙ | ⊙ |
| 300° C. × 20 min. | ⊙ | 3H | ⊙ | ⊙ | ⊙ |
| 350° C. × 20 min. | ⊙ | 3H | ⊙ | ⊙ | ⊙ |
| 400° C. × 20 min. | ⊙ | 3H | ⊙ | ⊙ | ⊙ |
| 420° C. × 20 min. | ⊙ | 4H | ⊙ | ⊙ | ○ |
| 450° C. × 20 min. | ⊙ | 5H | ⊙ | ⊙ | × |
| 500° C. × 20 min. | ⊙ | 6H | ⊙ | ⊙ | × |

TABLE 6

| | Binder | Deodorizing catalyst | | | | | | | | | Additives | | |
|---|---|---|---|---|---|---|---|---|---|---|---|---|---|
| | (8) | (6) | (15) | (16) | (20) | (23) | (37) | (45) | (67) | (72) | (1) | (10) | (11) |
| Blend Example (1) | 50 | 5 | 5 | 5 | 5 | — | — | — | — | — | 0.1 | 0.05 | 0.05 |
| Blend Example (2) | 50 | — | 5 | 5 | 5 | 5 | — | — | — | — | 0.1 | 0.05 | 0.05 |
| Blend Example (3) | 50 | — | — | 5 | 5 | 5 | 5 | — | — | — | 0.1 | 0.05 | 0.05 |
| Blend Example (4) | 50 | — | — | — | 5 | 5 | 5 | 5 | — | — | 0.1 | 0.05 | 0.05 |
| Blend Example (5) | 50 | — | — | — | — | 5 | 5 | 5 | 5 | — | 0.1 | 0.05 | 0.05 |
| Blend Example (6) | 50 | — | — | — | — | — | 5 | 5 | 5 | 5 | 0.1 | 0.05 | 0.05 |
| Blend Example (7) | 50 | — | 5 | 5 | 5 | — | — | 5 | — | — | 0.1 | 0.05 | 0.05 |
| Blend Example (8) | 50 | — | 5 | — | 5 | 5 | — | — | 5 | — | 0.1 | 0.05 | 0.05 |
| Blend Example (9) | 50 | 5 | — | 5 | — | 5 | — | 5 | — | — | 0.1 | 0.05 | 0.05 |
| Blend Example (10) | 50 | 5 | — | — | 5 | — | 5 | — | 5 | — | 0.1 | 0.05 | 0.05 |
| Blend Example (11) | 50 | — | 5 | 5 | — | 5 | — | 5 | — | — | 0.1 | 0.05 | 0.05 |
| Blend Example (12) | 50 | — | — | 5 | — | 5 | — | 5 | — | 5 | 0.1 | 0.05 | 0.05 |

We claim:

1. A deodorant composition, comprising a binder comprising an effective amount of an inorganic silicon compound; and a metal oxide or salt of at least one metal selected from the group consisting of titanium, lanthanum and manganese; or zirconium phosphate or a combination thereof, which deodorant comprises from 5 to 98 wt % of said binder, from 0.50 to 90 wt % of the metal oxide or salt, from 0 to 94.5 wt % of a colorant or a filler or both, and from 0 to 5 wt % of an additive.

2. The deodorant composition according to claim 1, wherein the additive is a fluorine-based wetting agent or an anti-settling agent or both, said anti-settling agent comprising polyethylene oxide or an organic amide.

3. The deodorant composition according to claim 1 wherein said metal oxide or salt is a mixture of titanium oxide and zirconium phosphate.

4. The deodorant composition according to claim 1, wherein said binder further comprises an organosilicon compound.

5. The deodorant composition according to claim 1, wherein the filler is used in an amount of form 0.01 to 19 parts by weight per 1 part by weight of the binder.

6. The deodorant composition according to claim 1, wherein the colorant is a black or red metal oxide colorant.

7. The deodorant composition according to claim 1, wherein said binder consists essentially of an inorganic silicon compound.

8. A deodorizing product, comprising the deodorant composition of claim 1 in an amount effective to effect deodorization of bad odors.

9. The deodorizing product of claim 1, wherein said bad odors comprise odors of trimethylamine, methyl mercaptan and hydrogen sulfide.

* * * * *